(12) United States Patent
Lin et al.

(10) Patent No.: US 8,182,831 B2
(45) Date of Patent: May 22, 2012

(54) STABLE AND TASTE MASKED PHARMACEUTICAL DOSAGE FORM USING POROUS APATITE GRAINS

(75) Inventors: Chang-Yi Lin, Kaohsiung (TW); Yunn-Tzer Lu, Yilan County (TW); Dean-Mo Liu, Hsinchu County (TW)

(73) Assignee: Nanotrend Ino-Tech Inc., Taipei (TW)

( * ) Notice: Subject to any disclaimer, the term of this patent is extended or adjusted under 35 U.S.C. 154(b) by 2477 days.

(21) Appl. No.: 10/800,622

(22) Filed: Mar. 16, 2004

(65) Prior Publication Data

US 2004/0180097 A1     Sep. 16, 2004

Related U.S. Application Data

(63) Continuation-in-part of application No. 10/386,546, filed on Mar. 13, 2003, now abandoned.

(51) Int. Cl.
  *A61F 13/00*  (2006.01)
  *A01K 31/715*  (2006.01)
  *A01N 43/04*  (2006.01)
(52) U.S. Cl. ............. 424/426; 514/54; 514/55; 514/57; 514/58
(58) Field of Classification Search .................. None
  See application file for complete search history.

(56) References Cited

U.S. PATENT DOCUMENTS

| 5,603,945 A | * | 2/1997 | Isobe et al. ................. 424/442 |
| 5,648,399 A | * | 7/1997 | Friedman et al. ........... 514/772.6 |
| 2003/0168401 A1 | * | 9/2003 | Koslow ..................... 210/500.25 |

FOREIGN PATENT DOCUMENTS

| EP | 0376331 | | 7/1990 |
| JP | 62032872 A | * | 2/1987 |
| JP | 2-200628 | | 8/1990 |
| JP | 6-298639 | | 10/1994 |
| JP | 2003-212756 | | 7/2003 |
| WO | WO 0015194 A1 | * | 3/2000 |

OTHER PUBLICATIONS

Makoto et al. "Effect of Sodium bicarbonate amount on in vitro indomethacin release from self-setting carbonated apatite cement", Pharmaceutical Research, vol. 14, No. 4, 1997.*

* cited by examiner

*Primary Examiner* — Michael G Hartley
*Assistant Examiner* — Nabila Ebrahim
(74) *Attorney, Agent, or Firm* — Bacon & Thomas, PLLC

(57) ABSTRACT

A stable and taste masked pharmaceutical dosage form includes porous apatite grains and a drug entrapped in pores of said grains, wherein said grains have a size of 0.1-1000 μm and said pores of said grains have an opening of 0.5-300 nm. A process for preparing the stable and taste masked pharmaceutical dosage form is also disclosed.

20 Claims, 5 Drawing Sheets

STABLE AND TASTE MASKED PHARMACEUTICAL DOSAGE FORM USING POROUS APATITE GRAINS

FIELD OF THE INVENTION

The present invention relates to a novel technique for encapsulating an unstable drug and/or a drug with unpleasant taste, and in particular by using porous apatite grains to entrap a drug in pores thereof.

BACKGROUND OF THE INVENTION

It has been known that a drug loaded calcium phosphate cement (CPC) block can be prepared by forming a CPC paste by mixing CPC powder and an aqueous setting solution together with a drug which may be in the form of a powder or as a solute of the solution, and molding and setting the paste into a block. The drug loaded CPC block is then implanted into a patient as a bone graft or bone substitute, so that the drug is slowly released from the block in the patient's body. Alternatively, the paste may be injected into a bone cavity or defect of a patient, which forms a hardened hydroxyapatite block in-situ. Typical examples may be found in U.S. Pat. No. 5,525,148, WO 98/16209, WO 98/16168 and WO 00/15194.

There is a long standing need for an stable and taste masked dosage form for a drug which is unstable in ambient and/or with an unpleasant taste in the pharmaceutical industry, so that the drug can be orally taken by the patients and stored for a desired period of time without substantially losing its potency. To name a few those drugs include ascorbic acid, aspirin, zinc gluconate and ibuprophen.

SUMMARY OF THE INVENTION

A primary object of the present invention is to provide a stable oral pharmaceutical dosage form.

Another object of the present invention is to provide a taste masked oral pharmaceutical dosage form.

Another object of the present invention is to provide a process for preparing a pharmaceutical dosage form which is stable in ambient and/or able to taste mask an unpleasant taste of a drug.

In order to achieve the aforesaid objects of the present invention, a technique disclosed in the present invention comprises mixing the powder precursors of the apatite, e.g. calcium source powder and phosphate source powder, in an inert liquid medium and granulating the resulting slurry, so that the resulting green granules are porous and substantially free of apatite phase, and trigging an apatite phase conversion reaction by adding water or an aqueous solution to the green granules while stirring or fluidizing, so that porous calcium phosphate-based apatite grains (hereinafter termed porous apatite grains) are formed. The drug can be incorporated to the porous apatite grains either in the inert liquid medium, e.g. the drug is soluble in the inert liquid medium, or in the water, e.g. the drug is water soluble. A straightforward way to incorporate a drug to the porous apatite grains is contacting blank porous apatite grains with a solution of the drug, and evaporating the solvent of the solution. It is believed that substantially all the drug is entrapped in pores of the porous apatite grains evidenced by a slow release of a water soluble drug loaded in the apatite grains in a phosphate-buffered solution.

DETAILED DESCRIPTION OF THE INVENTION

Figure 1:
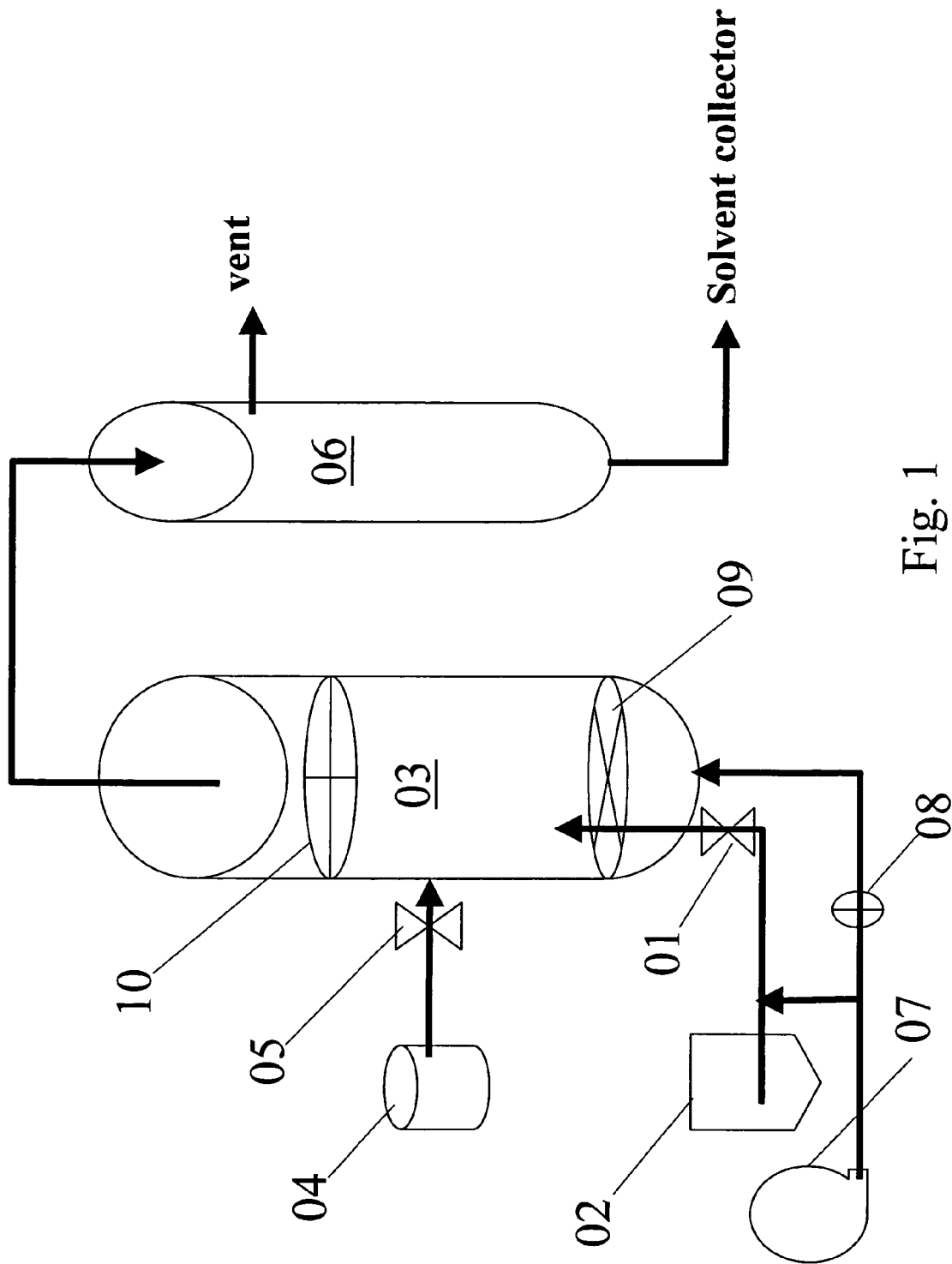
FIG. 1 is a schematic view of a home-designed fluidized reactor for use in the granulation and the conversion reaction to apatite phase according to the present invention.

The present invention discloses a stable and/or taste masked pharmaceutical dosage form comprising porous apatite grains and a drug entrapped in pores of said grains, wherein said grains have a size of 0.1-1000 µm, preferably 1 to 300 µm, and said pores of said grains have an opening of 0.5-300 nm, preferably 1 to 200 nm.

Preferably, said grains have a specific surface area of 32 to 58 $m^2$ per unit gram.

Preferably, said drug entrapped in said porous apatite grains is in an amount of 0.1-45%, more preferably 1-30%, based on the weight of the grains.

Preferably, the pharmaceutical dosage form of the present invention further comprising a water soluble polymer entrapped in pores of said grains in an amount of 0.1-10% based on the weight of the grains. Said water soluble polymer includes (but not limited to) chitosan, gelatin, agar, cellulose, chitin, starch, dextrin, cyclodextrin, polylactic acid, polyamino acid, polyethylene glycol, polyacrylates, hyaluronic acid, polyvinyl alcohol, povidone and mixture thereof. Preferably, said water soluble polymer is cellulose, polyethylene glycol, polyvinyl alcohol, or povidone.

Preferably, said apatite grains have a Ca to P molar ratio of 1.1 to 2.1, and more preferably 1.3 to 1.60.

Preferably, said apatite grains contains carbonate in an amount of 0.1-40% based on the weight of the grains.

Said drug may be a peptide, protein, enzyme, DNA, RNA, nutrient supplement agent, anti-inflammatory drug, anti-biotic drug, anti-histamine drug, anti-bacterial drug, anti-fungal drug, decongestant, anti-depressant, anti-psychotic drug, anti-viral drug, anti-oncolytic drug, vaccine, anti-epileptic drug, anti-asthma drug, antioxidant or extract of herb. To name a few, said drug is zinc gluconate, copper gluconate, carbinoxzmine maleate, dextromethorphan hydrobromide, glyceryl guaiacolate, pseudoephedrine hydrochloride, tripolidrine hydrochloride, acetaminophen, aspirin, ibuprophen, dexibuprophen lysinate, naproxen, ketoprofen, lactam, quinolone, macrolide or salts thereof, loperamide, famotidine, ranitidine, cimetidine or salts thereof, ibersartan, captopril, lisinopril or salts thereof, nefzodone, buspirone or salts thereof, chlorpheniramine, astemizole, pseudoephedrine, medicon, anpirin, actirin, nidolin, ascorbic acid, hydrocortisone, 5-fluorouracil, cis-platin, paclitaxel, ampicilin, cefadroxil, clindamycin, neomycin, nystatin, polyphenol, hydroquinone, or retinal A. Preferably, said drug is zinc gluconate, copper gluconate, aspirin, ibuprophen or ascorbic acid.

Preferably, the pharmaceutical dosage form of the present invention further comprises a biocompatible polymer, and said porous apatite grains are bound by said biocompatible polymer to form a microspherical composite having a size of 0.5-1000 μm. Said biocompatible polymer is preferably in an amount of 0.5% to 30% based on the weight of the grains. Said biocompatible polymer may be selected from polylactic acid, polyglycolic acid, poly(lactic-co-glycolic acid), polyanhydrates, polyethylene glycol, polyethylene oxide, polyacrylates, polymethacrylates, dextran, polysaccharides, hyaluronic acid, and mixture thereof. Among them polylactic acid, polyethylene glycol, and poly(lactic-co-glycolic acid) are preferred.

A suitable process for preparing the pharmaceutical dosage form of the present invention comprises the following steps:
a) mixing particles of a calcium source and particles of a phosphate source in a non-aqueous liquid medium, and optionally milling the resulting mixture, so that a slurry has a Ca/P ratio of 1.1-2.1 and particles suspended therein having a size of 0.01-20 μm;
b) adding a drug soluble in said non-aqueous liquid medium to the slurry;
c) granulating the slurry;
d) adding an aqueous solution of a drug or a drug-free aqueous solution to the resulting granules from step c);
e) stirring or fluidizing the wetted granules, so that porous apatite grains are formed, wherein said drug is entrapped in pores of said grains, wherein said grains has a size of 0.1-1000 μm and said pores of said grain have an opening of 0.5-300 nm,
wherein step b) may be omitted, when said aqueous solution of the drug in step d) is added to the resulting granules from step c).

Preferably, step a) further comprises mixing particles of carbonate source together with said particles of calcium source and phosphate source in an amount of 0.1-40% based on the total weight of said particles of calcium source and phosphate source.

Preferably, said non-aqueous liquid medium in step a) selected from the group consisting of methanol, ethanol, 1-propanol, 2-propanol, acetone, methyl ethyl ketone, toluene, ethyl acetate, butyl acetate, and a mixture thereof.

Preferably, said phosphate source in step a) is selected from the group consisting of magnesium phosphate, monocalcium phosphate anhydrate, dicalcium phosphate anhydrate, tricalcium phosphate, potassium dihydrogen phosphate, sodium dihydrogen phosphate, and a combination thereof.

Preferably, said calcium source in step a) is selected from the group consisting of calcium hydroxide, calcium chloride, calcium carbonate, and a combination thereof.

Preferably, said carbonate source in step a) is selected from the group consisting of calcium bicarbonate or sodium bicarbonate or potassium bicarbonate, and a combination thereof.

Preferably, the mixture of said particles has a Ca to P molar ratio of 1.1 to 2.1, and more preferably 1.3 to 1.60.

Preferably, said drug in step b) and said drug in step d) are in an amount of 0.1-45% based on the weight of the grains formed in step e).

Preferably, said granulating in step c) comprises atomizing said slurry and drying the resulting aerosol.

Preferably, said aqueous solution of the drug in step d) is sprayed to the resulting granules from step c), while stirring or fluidizing.

Preferably, said drug-free aqueous solution in step d) is sprayed to the resulting granules from step c), while stirring or fluidizing, wherein said drug-free aqueous solution is water, phosphate buffered aqueous solution (PBS), or HanK's solution.

Preferably, water contained in said aqueous solution of the drug and said drug-free aqueous solution in step d) added to the resulting granules from step c) is in a weight ratio of said water to the mixture of said particles of 0.05:1 to 0.30:1.

Preferably, said aqueous solution of the drug and said drug-free aqueous solution in step d) further comprises the above-mentioned water soluble polymer in an amount of 0.1-10% based on the weight of the mixture of said particles.

Preferably, step a) further comprises mixing the above-mentioned biocompatible polymer with said particles in an amount of 0.5-30% based on the total weight of said particles in said non-aqueous liquid medium, wherein said biocompatible polymer is soluble in said non-aqueous liquid medium, so that said porous apatite grains formed in step e) are bound by said biocompatible polymer to form a microspherical composite having a size of 0.5-1000 μm.

Preferably, the process of the present invention further comprises f) drying the porous apatite grains resulting from step e).

Said drug in step b) and said drug in step d) are the same as the drugs mentioned in the pharmaceutical dosage form of the present invention. A water soluble drug is suitable to be entrapped in the porous grains in the form of an aqueous solution, for example zinc gluconate, copper gluconate, salts of zinc, salts of copper, salts of iron, ascorbic acid, peptide, protein, enzyme, DNA, RNA, nutrient supplement agent, anti-inflammatory drug, anti-biotic drug, anti-histamine drug, anti-bacterial drug, anti-fungal drug, decongestant, anti-depressant, anti-psychotic drug, anti-viral drug, anti-oncolytic drug, vaccine, anti-epileptic drug, anti-asthma drug, antioxidant, water soluble vitamins or extract of herb. A drug soluble in the non-aqueous liquid medium in step a) can be entrapped in the porous grains via step b), for example ibuprophen, aspirin, nutrient supplement agent, anti-inflammatory drug, anti-biotic drug, anti-histamine drug, anti-bacterial drug, anti-fungal drug, decongestant, anti-depressant, anti-psychotic drug, anti-viral drug, anti-oncolytic drug, anti-epileptic drug, anti-asthma drug, antioxidant, oil-soluble vitamins or extract of herb.

An alternative process for preparing pharmaceutical dosage form of the present invention is similar to the above-mentioned process except that the drug is post added. In this alternative process blank porous apatite grains are formed by omitting step b) and by adding the drug-free aqueous solution in step d) to the resulting granules from step c); a drug in the form of a solution is added to the blank porous apatite grains; and dry the solution so that said drug is entrapped in pores of said grains.

In one of the preferred embodiments of the present invention, the process developed was carried out in a home-designed fluidized reactor, as schematically illustrated in FIG. 1. Said slurry is fed from tank 02 through a nozzle atomizer 01 into chamber 03, wherein the temperature of the chamber 03 is controlled at a range from 25 to 60 degrees of Celsius by a heated (via heater 08) flowing air (via air compressor 07). Powder granules developed instantly after the liquid medium is removed and collected in the bottom of a condenser 06. Air is vented from the top of the condenser 06. In the meantime, the solid granules are fluidized in the chamber 03 as a result of flowing air through the air distributor 09. A filter 10 is placed on the top of the chamber 03 to prevent the loss of the powder granules. The powder granules are kept fluidizing until being dried.

The powder granules are spherelike geometry, having a size ranging from 1 to 300 micrometers, or more preferably, in the size of 1 to 100 micrometers in diameter. After the said powder granules were formed, water or preferably, a phosphate-buffered solution (PBS) at a pH value of 6.8-10.5, is fed from tank 04 through a nozzle atomizer 05 to coat the said powder granules in the chamber 03 with a thin layer of water film, to uniformly wet the powder granules and at the same time, to trigger neutralization reaction in each individual powder granule. In this invention, the weight ratio of powder-to-water is in the range from 1:0.05 to 1:0.35, or in a preferred embodiment, in the range of 1:0.05 to 1:0.30. Such a preferred amount of water or PBS used is considerably lower than those disclosed known in the art. During the water or PBS coating process, the chamber 03 is kept at ambient temperature and the powder granules are under fluidizing.

After the incorporation of water or PBS, the resulting phase-pure apatitic phase can be obtained in few minutes to a couple of hours, depending on the amount and pH of the said water or PBS addition, and the composition of the apatite precursor. A faster neutralization reaction (apatite phase conversion reaction) can be proceeded and completed for a power-to-water weight ratio greater than 1:0.18, wherein the said neutralization reaction taking place within the powder granules can be achieved in 5-10 minutes. However, below the ratio of 1:0.18, the said neutralization reaction can be sustained as long as couple of hours. This is because of the water or PBS is acting as one of the reactants in the said neutralization reaction, a smaller amount of the water or PBS can thus result in a slower kinetics in the said reaction. It is also found to be undesirable for the water or PBS addition greater than the said ratio of 1:0.35, since undesirable phenomena such as powder agglomeration, caking, weaker strength of the resulting microcapsules, prolong time for water removing stage, making the production process more cost-ineffective and time consuming.

The pH value of said water or PBS is preferably in the range of 7.0 to 9.0, which is closer to that of physiological condition. After neutralization reaction is completed, the flowing air is further heated to a temperature from 30 to 40 degrees of Celsius to remove extra water that is produced as a by-product of the neutralization reaction within the powder granules. In this invention, a preferred water concentration in the porous apatite grains is between 0 to 10 weight percent, or more preferably, in the range of 0 to 5 weight percent, or most preferably, in the range of 0 to 2 weight percent, wherein the water is allowed to exist as a result of surface adsorption from the air moisture. A minimal amount of water, or preferably free of water, is suitable for those vulnerable drugs.

One unique advantage of the process disclosed in this invention is that the time period of phase conversion upon water or PBS addition can be largely reduced, typically in 5-10 minutes, wherein the aforesaid powder granules prepared according to this invention can be rapidly hardened, in comparison to those similar calcium phosphate-based cement materials described in literature, wherein a phase conversion to hardening taking 24 hours or even longer is reported. It is important to emphasize the rapid hardening of the said calcium phosphate composition, wherein the drug or active agent is expected to freeze in place due to the development of nanostructured apatitic phase. In a preferred embodiment of this invention, the resulting pore size as determined by the BET has a range of 0.5 to 50 nm and a mean pore size of 5.7 nm, suggesting the drug molecule can be effectively and physically constraint in a nanometric space. Such nanometric voids developed in the porous apatite grains are effectively retained the biological and/or therapeutical activity of the drugs after administrated orally or intravenously.

Figure 2:
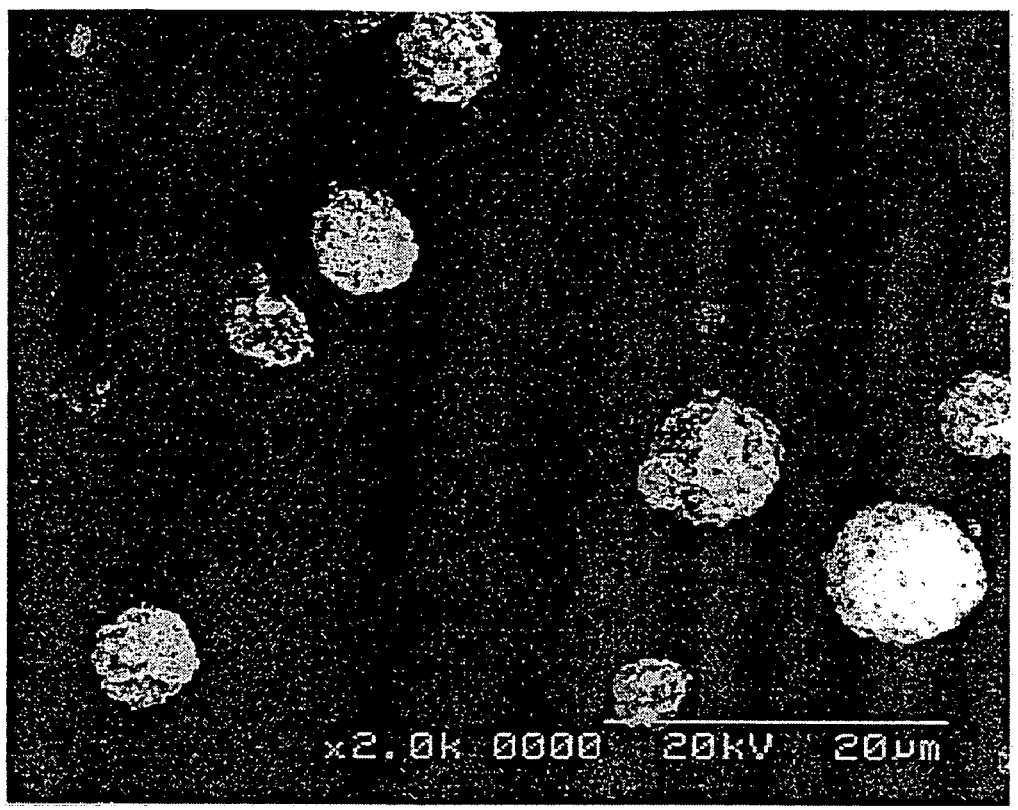
FIG. 2 is a SEM picture showing morphology of the microspherical composites of porous apatite grains and poly(DL-lactic-co-glycolic) acid, having a size of about 2-5 µm in diameter.

In one aspect of the present invention a microspherical composite of apatite grains and polymer is prepared. According to another one of the preferred embodiments of the present invention, a slurry containing monocalcium phosphate anhydrate or dicalcium phosphate powder, sodium phosphate, calcium hydroxide, calcium bicarbonate, and 12% by weight of polylactic acid (PLA) was prepared via ball milling. The Ca/P ratio of the starting inorganic powder is fixed at 1.5. The micrometric granules were developed via a simple spray dry, where the resulting granules have a size ranging from 0.5 to 1,000 μm diameter. As shown in FIG. 2, a phase-pure, poorly crystalline, calcium-deficient carbonated apatite (cHA)—polymer composite develops successfully after 8 h exposure with moisture. The presence of polymer provides strong bond to retain mechanical and structural integrity of the granules during subsequent handling. The inorganic component shows a nano-structured morphology, with a grain size below 100 nm, which is essentially chemically and structurally similar to that of biological apatite. The polymer component, which is also biodegradable, is simulating that of organic content in the bone tissues in human and vertebrates. The pore analysis of the granules, as determined by the BET method, shows a pore size distribution ranging dominantly in the range of 1 nm to 200 nm. The mineralization process during synthesis under humid atmosphere, i.e., vapor water, may be grossly expressed as a result of interaction among the starting inorganic powder mixture as employed in this example,

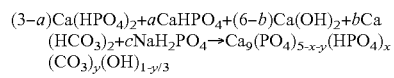

$$(3-a)Ca(HPO_4)_2 + aCaHPO_4 + (6-b)Ca(OH)_2 + bCa(HCO_3)_2 + cNaH_2PO_4 \rightarrow Ca_9(PO_4)_{5-x-y}(HPO_4)_x(CO_3)_y(OH)_{1-y/3}$$

where a has a value ranging from 0 to 1.6, and b has a value ranging from 0 to 6, and c, from 0.1 to 0.4. The carbonate ions can be replaced either OH or $PO_4$ groups, or both in the apatitic lattice, resulting in, as the case of present composition, an AB-type carbonated apatite.

Figure 3:
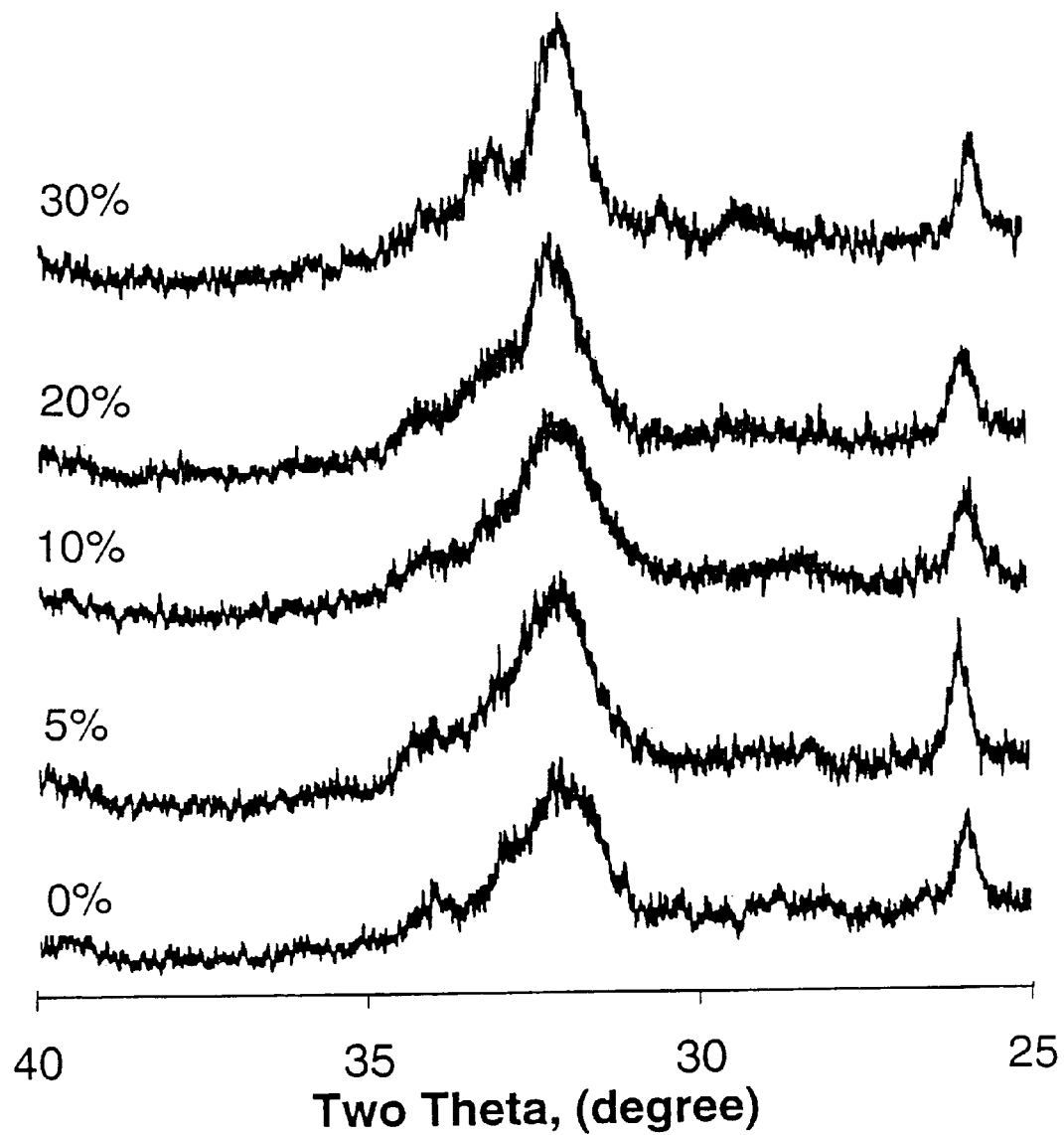
FIG. 3 shows X-ray diffraction patterns of carbonated apatite (cHA) containing different amounts of carbonate ranging from 0% to 30% by weight.
Figure 4:
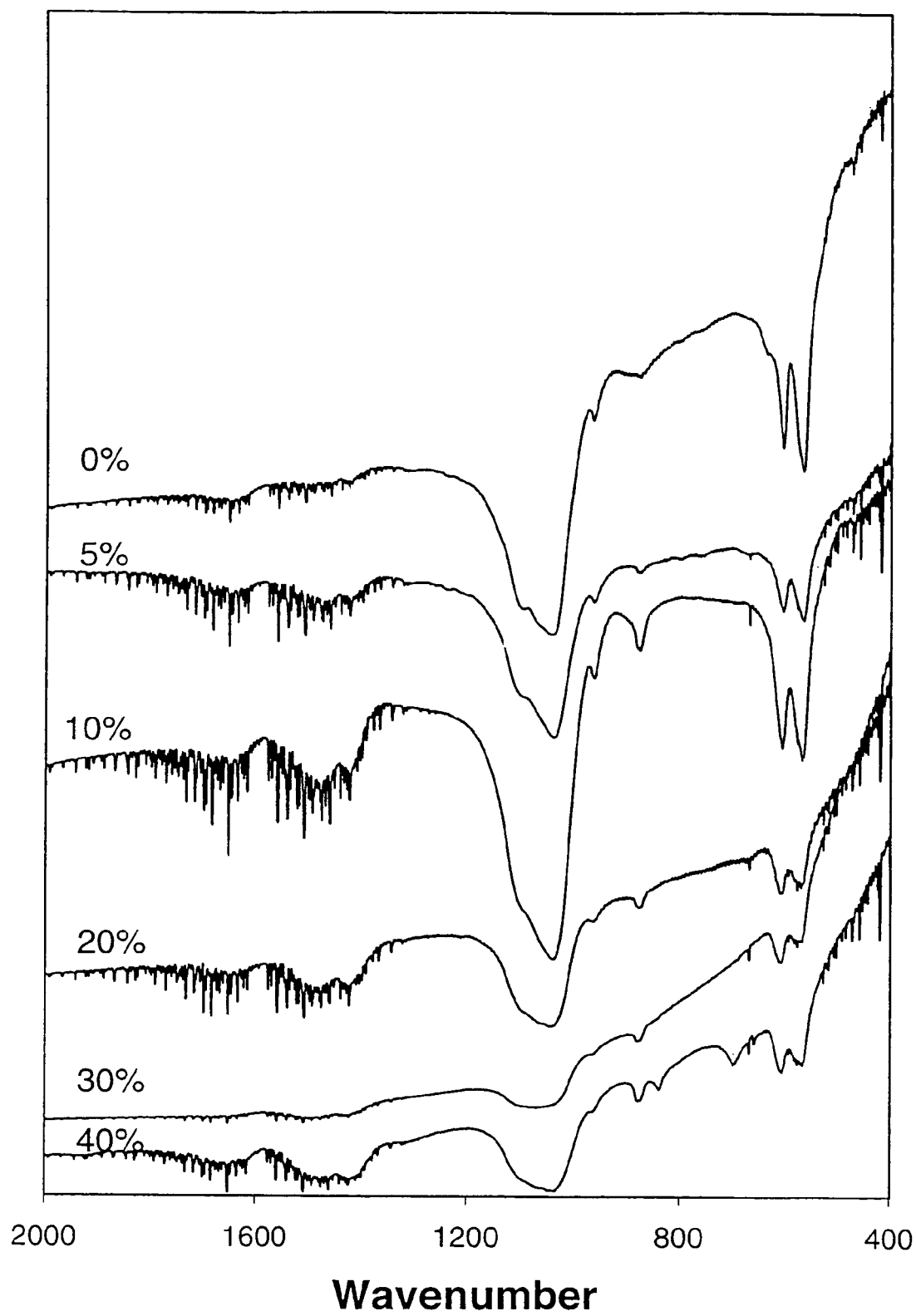
FIG. 4 shows Fourier transform infrared spectra of the cHA containing different amounts of carbonate ranging from 0% to 40% by weight.

In the present invention, a composition is provided to form cHA with controllable concentration of carbonate, ranging from 0% to 40% by weight. The cHA showed phase-pure and poorly-crystalline structure as evidenced from an X-ray diffraction analysis (XRD, FIG. 3), whereas no residual impurity phases, such as carbonate or calcium phosphate precursors were detectable under the resolution of the XRD. Fourier transformed infrared spectrum analysis (FTIR, FIG. 4) shows two absorption bands at 562 $cm^{-1}$ and 600 $cm^{-1}$, together with a broad band in the region of 1,100-1,000 $cm^{-1}$, indicating a typical apatitic structure. Bands at 871 $cm^{-1}$ and 1430 $cm^{-1}$ indicate the presence of $CO_3$ groups in the apatitic structure. Both $CO_3$ bands suggest that the apatite obtained in this composition is AB-type carbonated apatite. Increase in carbonate concentration suggests sufficient amount of the carbonate ions being incorporated into the apatitic lattice.

By proper control of the carbonate content, from low (less resorable in physiological environment) to high concentration (easily resorable), the dissolution behavior of the final cHA allows to be finely tuned for application-oriented customization.

In this invention, dicalcium phosphate (DCP), $CaHPO_4$, is synthesized through a simple co-precipitation method. A combination of commercially available calcium hydroxide and monocalcium phosphate monohydrate, or ammonium hydrogen phosphate, or phosphoric acid allows nanometer-size DCP particles to be synthesized by first adding small amount, say 0.1%-10%, or more preferably, 0.5%-5% by weight, of water-soluble surfactants including citric acid and/or polyacrylic acid into aqueous calcium hydroxide solution. The fine dicalcium phosphate crystals precipitate immediately upon an acidic phosphate solution being added via titration. The precipitates are separately right after the completion of the titration through a filter paper. To remove the surfactant, the filtered powder cake is further rinsed several times with large quantity of distill water, following oven drying at a temperature of 150-180° C. The resulting powders, which show a diffraction pattern exactly the same as the DCP powder indexed by the Joint Committee Powder Diffraction Standard card, show a uni-model particle size distribution with an average particle size between 0.02 um to 2 um, depending upon the concentration of the surfactant used.

The other inorganic ingredients such as monocalcium phosphate anhydrate, sodium phoshate, calcium hydroxide, calcium bicarbonate or sodium bicarbonate are used as commercially available. However, a vigorously milling by, but not limited to, ball miller, attrition miller, rotary miller, is used for reduction of the particles to a size ranging from 0.01-20 μm, preferably 0.05-2 μm, or more preferably, 0.05-1 μm. In addition, the nanometer-to-submicrometer particle size of the inorganic powders promotes phase transformation towards final apatitic structure, accompanied with hardening of the cHA. However, measurement of the harding time (ISO1566) was found to increase with carbonate concentration, from 5-20 min for <10% carbonate, to as high as 120-150 min for $\geq$30% carbonate.

The invention will be more fully understood from the following examples, all of which are used only for illustrative purposes and not intended in any way to limit the invention.

Example 1

Drug Loaded Microcapsules, Apatite Grains

A power mixture containing 52.3 g of magnesium phosphate, 234.05 g of monocalcium phosphate anhydrate, 27.2 g of potassium dihydrogen phosphate, 194.25 grams of calcium hydroxide, and 35.8 g of magnesium hydroxide was prepared into a slurry with methanol as a diluting medium. The total weigh of the starting powder is 543.6 grams in this study, wherein the Ca/P ratio in the starting powder mixture is designed to be 1.45. The slurry was subject to extensive grinding using an attrition miller for 10 hours, resulting in an average particle size of 106 nanometers in diameter. The as-prepared slurry was then subject to granulation via the home-designed fluidized reactor shown in FIG. 1.

Two aqueous solutions with a pre-determined amount, relative to 30 weight percent of the starting inorganic mixture, of nutrient supplements, namely, zinc gluconate and copper gluconate were prepared separately by dissolving into phosphate-buffered solution (PBS). The said zinc gluconate and copper gluconate are known to be food supplement and possess unpleasant taste. About 30 minutes after the granulation was completed, the calcium phosphate-based powder granules were subject to mix with the drug-containing PBS via a further atomization of the PBS into the fluidizing powder granules. Upon PBS addition, the fluidized reactor was kept at room temperature and the powder granules were continuously subjecting to fluidize for 12 minutes. The final powder microcapsules were collected. The encapsulation efficiency of the zinc gluconate and copper gluconate within the said microcapsules was estimated by measuring the concentration of the supplements in the microcapsules via an atomic absorption spectrometry and is listed in Table 1 wherein an efficiency greater than 99% was obtained.

TABLE 1

Encapsulation efficiency of the nutrient supplements within the said microcapsules via the production process disclosed in this invention.

| Supplements | Pre-determined amount (wt %) | Measured amount in microcapsule (wt %) | Efficiency (%) |
| --- | --- | --- | --- |
| Zinc gluconate | 30 | 30.1 | 100 |
| Copper gluconate | 30 | 29.8 | 99.3 |

A direct taste of the encapsulated metal gluconates via oral administration was performed and no any unpleasant taste was exposed in the mouth, in comparison to that taken directly with the metal gluconates.

Example 2

Drug Loaded Microcapsules, Apatite Grains

A powder mixture containing 17.43 g of magnesium metaphosphate, 117.03 g of monocalcium phosphate anhydrate, 40.83 g of potassium dihydrogen phosphate, 116.2 g of calcium hydroxide, and 10 g of calcium carbonate, was prepared into a slurry with a mixture solvent of acetone and ethanol as a diluting medium. The total weigh of the starting powder is 301.5 grams in this study, wherein the Ca/P ratio in the starting powder mixture is 1.55. The slurry was subject to extensive grinding using an attrition miller for 24 hours, resulting in an average particle size of 95 nanometers in diameter. The calcium carbonate powder employed is in nanometric scale, having a particle size of 7-10 nanometers in diameter.

After the said slurry was prepared, a small amount of ibuprophen powder was added into the slurry and gently stirring, then, the final slurry was subject to a granulation stage according to Example 1. After the slurry was dried into granules of size from 30 to 150 micrometers, a small amount of polyethylene glycol-containing (corresponding to 3 weight percent to the final microcapsules) water was atomized and mixed with the fluidizing powder granules. The ibuprophen is known to have a bad taste and hard to swallow directly or using chewable tablet for patients. The ibuprophen with 10 wt % relative to the starting powder mixture was used and the water used has a weight ratio to the starting powder of 0.2:1. After water was incorporated, the starting calcium phosphate granules were hardened and converted into an apatitic phase as detected by X-ray diffraction analysis at a time period as short as about 6 minutes. The ibuprophen to be encapsulated has an amount of 9.85% in the final microcapsules, indicating an encapsulation efficiency as high as 99%. The bad taste of the bare ibuprophen, when orally administrated, was completely removed via the said calcium phosphate apatitic microcapsules. This test has further confirmed an efficient taste masking effect of the said microcapsules can be attained, and the final microcapsules were further assembled into small tablet suitable for oral swallowing.

Example 3

Drug Loaded Microcapsules, Apatite Grains

Powder mixture according to Example 2 was prepared into spherical powder granules via the said home-designed fluidized reactor. Ascorbic acid with an amount of 2.2 weight percent relative to the powder granules was dissolved in water. The powder-to-water ration is 1:0.25 in this evaluating test. The ascorbic acid-containing water was atomized via nozzle sprayer into the fluidized reactor while the powder granules were under fluidizing. The final ascorbic acid-containing apatite microcapsules were further assembled into tablet of 1500 mg each via a conventional compressive tabulation process, which contained about 500 mg of the microcapsules, and 50 mg Mg as MgO among other ingredients. A controlled group of tablets prepared with a powder mixture of blank microcapsules and 2.2 weight percent of the ascorbic acid powder based on the weight of the blank microcapsules via the same tabulation process, wherein the blank microcapsules were prepared similarly to the drug-loaded microcapsules except the ascorbic acid-containing water was replaced by pure water.

The stabilization test was performed by incubating the tablets, together with a controlled group. The temperature was controlled at 40 degrees of Celsius and the relative humidity was 75 percent. Numerous brownish spots appeared on the white tablets of the control group for a test period of only 8 hours; however, for those tablets with ascorbic acid being encapsulated into the said microcapsules, the white appearance remained unchanged after at least 4 weeks incubation. This test strongly indicated the ascorbic acid, which is known to be easily oxidized in the presence of moisture and oxygen, has been well stabilized using the said microcapsules disclosed in this invention.

Example 4

Drug Loaded Microcapsules, Apatite Grains

Powder mixture with a composition according to Example 2 was prepared. Before granulation is conducted, dextromethorphan hydrobromide with a concentration of 30 weight percent relative to the starting powder was added and gently stirred for 30 minutes. The resulting slurry was then subject to spray drying via a 1-mm nozzle, wherein resulting powder granules with a size from 10 to 50 micrometers were obtained. Small amount of water was prepared, which contained 5 weight percent of agar, and atomized coating onto the fluidizing powder granules.

The resulting drug-containing microcapsules were further prepared into a dilute suspension and stored at room temperature for 7 days for a storage study. The test results showed little release of the dextromethorphan hydrobromide for the time period of study and the taste was not bitter. This study indicated the calcium phosphate apatite microcapsule prepared in this invention is able to effectively act as a taste masking vehicle for those drugs with unpleasant taste but also keep the product-type suspension stable for a long time period of storage.

Example 5

Microspherical Composite of Apatite Grains and Polymer

Powder slurry containing 187.2 grams of monocalcium phosphate anhydrate (may be replaced by 217.7 grams of dicalcium phosphate), 15.6 grams of sodium dihydrogen phosphate, 112.48 grams of calcium hydroxide, 23.4 grams of calcium carbonate was prepared in an ethanol-acetone mixture via ball milling for 24 hours, wherein 4.5 weight percent, relative to the powder, of polylactic acid (PLA) was added. The Ca/P ratio in the starting inorganic powder is fixed at 1.5. Dry granules with a size ranging from 10 to 150 μm diameter were obtained by using the fluidized reactor shown in FIG. 1. A small amount of water with a weight ratio to the starting powder of 0.35:1 was immediately mixed with the fluidizing powder granules. Apatitic phase appeared in about 15 minutes after water addition into the granules. The final microspherical composite shows a nano-structured morphology, with a grain size in the order of 100-150 nm, which is essentially chemically and structurally similar to that of biological apatite. The polymer component, which is also biodegradable, is simulating that of organic content in the bone tissues in human and vertebrates. The pore analysis of the composites, as determined by the BET sorption method, shows a pore size distribution ranging dominantly in the range of 1 nm to 200 nm.

Example 6

Microspherical Composites of Apatite Grains and Polymer

A series of powder mixtures containing fixed amount: 108.85 grams of dicalcium phosphate anhydrate, 93.6 grams of monocalcium phosphate anhydrate, 31.2 grams of sodium dihydrogen phosphate, 91.02 grams of calcium hydroxide, and 29.17 grams of magnesium hydroxide was prepared into a slurry with acetone as a diluting medium. The total weigh of the starting powder is 358.84 grams in this study, wherein the Ca/P ratio in the starting powder mixture is designed to be 1.35. Polylactic acid (PLA) polymer in an amount of 0.1, 0.3, 0.5, 1.2, 3, 5, and 7 weight percent relative to the total weight of the powder was added into the slurry, respectively. The slurry was subject to extensive grinding using a ball miller for 24 hours, resulting in an average particle size of 330 nanometers in diameter.

The slurry was spray dried into granules of size from 5 to 50 micrometers using the fluidized reactor shown in FIG. 1, a small amount of water with a weight ratio to the starting powder of 0.35:1 was immediately mixed with the fluidizing powder granules. Apatitic phase can be detected after 30-60 minutes of incubation in ambient, depending on the amount of PLA polymer. The higher concentration of the PLA concentration, the longer time for apatitic phase formation. It was found for the polymer concentration below 0.5 weight percent where a certain amount of fractured granules was observed, when an extensive fluidization was carried out, e.g. more than 20 minutes after addition of water. This suggests a need to reduce the fluidizing time when the polymer concentration is below 0.5 weight percent.

Example 7

Microspherical Composites of Apatite Grains and Polymer

Powder mixture containing 155.1 grams of tricalcium phosphate, 351 grams of monocalcium phosphate anhydrate, 54.4 grams of potassium dihydrogen phosphate, 229.4 grams of calcium hydroxide, and 50 grams of calcium carbonate was prepared into a slurry with acetone as a diluting medium. The total weight of the starting powder is 839.9 grams in this study, wherein the Ca/P ratio in the starting powder mixture is designed to be 1.50. Polyethylene glycol (PEG) polymer in an amount of 7 weight percent relative to the total weight of the powder was added into the slurry. The slurry was subject to extensive grinding using a ball miller for 24 hours, resulting in an average particle size of 210 nanometers in diameter.

The slurry was spray dried into granules of size from 30 to 250 micrometers by using the fluidized reactor shown in FIG. 1, a small amount of water with a weight ratio to the starting powder of 0.45:1 was immediately mixed with the fluidizing powder granules. Apatitic phase can be detected in the resulting microspherical composite after 30 minutes of incubation in ambient. However, it took about 2 hours to complete the phase conversion of the microspherical composite to form apatite when the granules were collected and stored in ambient environment. The incorporation of the calcium carbonate into the final apatitic grains suggests that the final apatitic grains is a type of carbonated calcium-deficient apatite. The resulting microspherical composite of apatitic grains and polymer were further dried in an oven for a time period of 24 hours to remove residual water.

The blank microspherical composites prepared in Examples 5-7 can be used as a carrier for drug microcapsulation by contacting a solution of drug with the blank microspherical composites and removing a solvent of the solution from the microspherical composites by evaporation. Preferably, the solution is atomized to the microspherical composites fluidizing in the reactor shown in FIG. 1.

Example 8

Consolidation of Microspherical Composite

A green microspherial composite (with 10% of potassium carbonate concentration) containing 20% by weight of polyethylene glycol (FCC grade, Union Carbide, USA) were prepared through spray dry. The green microspherical composite with approximately 0.5 g were compacted into a stainless steel die of 10 mm in diameter, following a uni-axial compression to 1 MPa. Thin pellets were developed and the relative density of the pellets is about 54-56%. The pellets showed soft feature when they was indented by the needle which is used for setting time measurement. The pellets were stored in an incubator with 100% relative humidity at 37° C. and, and the pellets hardened after 20-30 minutes in the incubator.

Example 9

Drug Release Study of Drug Loaded Microspherical Composite

Figure 5:
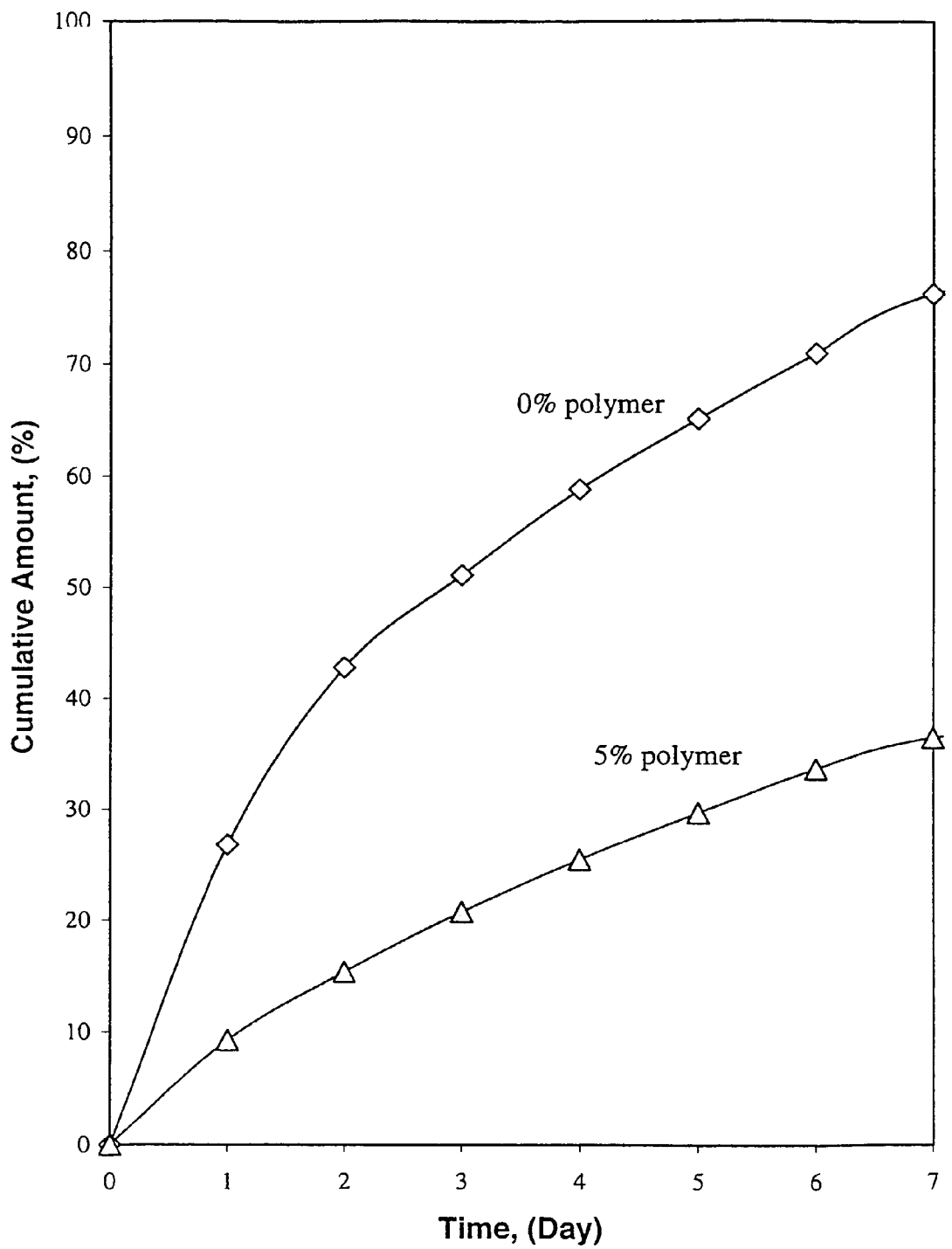
FIG. 5 is a plot showing release behavior of a model drug (5% by weight of fluorescein dye) from pellets containing porous apatite grains into a phosphate-buffered saline at 37° C. A sustain release for over 2 months was observed for pellets containing 5% PLGA; however, for those without incorportating polymers, approximately 20 days of release was observed.

A green microspherical composite containing 5% by weight of poly(lactic-co-glycolic acid) (PLGA) was prepared through spray dry. 5% (relative to the total weight of dried microspheres after encapsulation) fluorescein dye (sodium derivatives, JT Baker Chemicals Co., USA) dissolved in water as model drug (an imaging agent) was then slowly added into the prepared green microspherical composite with sufficient mixing. Pellets were prepared with the method described in Example 8. The pellets having a diameter of 10 mm and thickness of 0.5 mm, were subject to a release study by immersion into a phosphate-buffered saline (PBS at pH7.4) at constant weight (of the pellet)/volume (of the PBS) ratio of 0.5 mg/ml. Entire liquid samples were taken out and refilled with the same amount in a periodical manner. The concentration of the model drug in the supernatant was determined via a UV-Visible spectroscopy. The release kinetics is illustrated in FIG. 5 for the first 7 days; however, a sustain release over 2 months was detected. In addition, release behavior, for the first 7 days, was also measured for the pellets prepared from microspheres containing no polymer. A sustain release for a shorter time period, approximately 20 days, than the one with polymer was observed. The initial burst effect, which is detrimental to some medical application, can be reduced (or adjustable) to a considerable extent when the polymer phase was incorporated, which suggests to be a membrane effect that inhibits the initial fast release of the encapsulated model drug.

Example 10

Drug Release Study of Drug Loaded Microspherical Composite

Colloidal suspension was prepared according to the procedures described in Example 5, except that 10% polyethylene glycol was incorporated. 5% (relative to the total weight of solid content of the suspension after drug addition) amethopterin (Sigma, USA) as model drug dissolved in water was then added into the suspension and an emulsification process was immediately followed. The resulting microspherical composite was separated through a paper filter after vacuum evaporation, and stored in an incubator of 80-100% relative humidity at 40° C. for 16 hours. The amethopterin-contained microspherical composite of 50-200 μm in diameter was collected and subjected to drug release study with a procedure as described in Example 9. A sustain release with a behavior similar to the one with polymer in FIG. 5 over a time period of 2 weeks was detected.

Example 11

Protein Encapsulation using Microspherical Composite, and Activity

Colloidal suspension was prepared according to the procedure described in Example 5, where 5% PLGA (85/15) (a copolymer consisting 85% polylactic acid and 15% polyglycolic acid) was incorporated. 5% (relative to the total weight of solid content of the suspension after drug addition) bovine serum albumin (BSA, Sigma, USA) as model drug was then added into the suspension and an emulsification process was immediately followed with a mild rotating speed. The resulting protein loaded microspherical composite was spray dried and was subjected to drug release study. After a 24-h release into phosphate-buffered saline (PBS) at pH 7.4, the resulting supernatant was withdrawn and examined with UV-Visible spectroscopy at an absorbance peak of 220 nm. Little or no considerable difference in the UV-Visible spectra between the supernatant and a blank PBS was observed, suggesting conformational retention of BSA. This, according to the literature, further suggests sufficient retention of protein activity.

What is claimed is:

1. A stable and taste masked pharmaceutical dosage form comprising porous apatite grains and a drug entrapped in pores of said grains, wherein said grains have a size of 0.1-1000 μm and said pores of said grains have an opening of 0.5-300 nm, and said dosage form further comprising a biocompatible polymer, wherein said porous apatite grains are bound by said biocompatible polymer to form a microspherical composite having a size of 0.5-1000 μm.

2. The pharmaceutical dosage form according to claim 1 further comprising a water soluble polymer entrapped in pores of said grains in an amount of 0.1-10% based on the weight of the grains.

3. The pharmaceutical dosage form according to claim 1, wherein said grains have a size of 1 to 300 μm.

4. The pharmaceutical dosage form according to claim 1, wherein said pores have an opening of 1 to 200 nm.

5. The pharmaceutical dosage form according to claim 1, wherein said grains have a specific surface area of 32 to 58 m² per unit gram.

6. The pharmaceutical dosage form according to claim 1, wherein said drug entrapped in said porous apatite grains is in an amount of 0.1-45% based on the weight of the grains.

7. The pharmaceutical dosage form according to claim 6, wherein said drug entrapped in said porous apatite grains is in an amount of 1-30% based on the weight of the grains.

8. The pharmaceutical dosage form according to claim 2, wherein said water soluble polymer is selected from the group consisting of chitosan, gelatin, agar, cellulose, chitin, starch, dextrin, cyclodextrin, polylactic acid, polyamino acid, polyethylene glycol, polyacrylates, hyaluronic acid, polyvinyl alcohol, povidone and mixture thereof.

9. The pharmaceutical dosage form according to claim 8, wherein said water soluble polymer is cellulose, polyethylene glycol, polyvinyl alcohol, or povidone.

10. The pharmaceutical dosage form according to claim 1, wherein said apatite grains have a Ca to P molar ratio of 1.1 to 2.1.

11. The pharmaceutical dosage form according to claim 10, wherein said apatite grains have a Ca to P molar ratio of 1.3 to 1.60.

12. The pharmaceutical dosage form according to claim 1, wherein said apatite grains contains carbonate in an amount of 0.1-40% based on the weight of the grains.

13. The pharmaceutical dosage form according to claim 12, wherein said apatite grains have a Ca to P molar ratio of 1.3 to 1.60.

14. The pharmaceutical dosage form according to claim 1, wherein said drug is a peptide, protein, enzyme, DNA, RNA, nutrient supplement agent, anti-inflammatory drug, anti-biotic drug, anti-histamine drug, anti-bacterial drug, anti-fungal drug, decongestant, anti-depressant, anti-psychotic drug, anti-viral drug, anti-oncolytic drug, vaccine, anti-epileptic drug, anti-asthma drug, antioxidant or extract of herb.

15. The pharmaceutical dosage form according to claim 1, wherein said drug is selected from a group of zinc gluconate, copper gluconate, carbinoxzmine maleate, dextromethorphan hydrobromide, glyceryl guaiacolate, pseudoephedrine hydrochloride, triprolidrine hydrochloride, acetaminophen, aspirin, ibuprophen, dexibuprophen lysinate, naproxen, ketoprofen, lactam, quinolone, macrolide or salts thereof, loperamide, famotidine, ranitidine, cimetidine or salts thereof, ibersartan, captopril, lisinopril or salts thereof, nefzodone, buspirone or salts thereof, chlorpheniramine, astemizole, pseudoephedrine, medicon, anpirin, actirin, nidolin, ascorbic acid, hydrocortisone, 5-fluorouracil, cis-platin, paclitaxel, ampicilin, cefadroxil, clindamycin, neomycin, nystatin, polyphenol, hydroquinone, and retinal A.

16. The pharmaceutical dosage form according to claim 15, wherein said drug is zinc gluconate, copper gluconate, aspirin, ibuprophen or ascorbic acid.

17. The pharmaceutical dosage form according to claim 1, wherein said biocompatible polymer is in an amount of 0.5% to 30% based on the weight of the grains.

18. The pharmaceutical dosage form according to claim 1, wherein said biocompatible polymer is selected from the group consisting of polylactic acid, polyglycolic acid, poly (lactic-co-glycolic acid), polyanhydrates, polyethylene glycol, polyethylene oxide, polyacrylates, polymethacrylates, dextran, polysaccharides, hyaluronic acid, and mixture thereof.

19. The pharmaceutical dosage form according to claim 18, wherein said biocompatible polymer is polylactic acid, polyethylene glycol, or poly(lactic-co-glycolic acid).

20. The pharmaceutical dosage form according to claim 2, wherein said grains have a size of 1 to 300 μm; said pores have an opening of 1 to 200 nm, said grains have a specific surface area of 32 to 58 m² per unit gram, said drug entrapped in said porous apatite grains is in an amount of 1-30% based on the weight of the grains, wherein said water soluble polymer is cellulose, polyethylene glycol, polyvinyl alcohol, or povidone; and wherein said apatite grains have a Ca to P molar ratio of 1.3 to 1.60.

* * * * *